(12) United States Patent
Boyce et al.

(10) Patent No.: US 11,688,294 B2
(45) Date of Patent: Jun. 27, 2023

(54) SIMPLIFIED, INTERACTIVE, REAL-TIME ULTRASOUND BIOFEEDBACK SYSTEM FOR SPEECH REMEDIATION

(71) Applicant: UNIVERSITY OF CINCINNATI, Cincinnati, OH (US)

(72) Inventors: Suzanne Boyce, Cincinnati, OH (US); Sarah Hamilton Dugan, Dayton, OH (US); T. Douglas Mast, Cincinnati, OH (US); Michael Riley, Cincinnati, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 263 days.

(21) Appl. No.: 16/955,120

(22) PCT Filed: Dec. 21, 2018

(86) PCT No.: PCT/US2018/067018
§ 371 (c)(1),
(2) Date: Jun. 18, 2020

(87) PCT Pub. No.: WO2019/126611
PCT Pub. Date: Jun. 27, 2019

(65) Prior Publication Data
US 2020/0306565 A1    Oct. 1, 2020

Related U.S. Application Data

(60) Provisional application No. 62/609,356, filed on Dec. 22, 2017.

(51) Int. Cl.
*G09B 5/06*    (2006.01)
*G06T 5/00*    (2006.01)
(Continued)

(52) U.S. Cl.
CPC .............. *G09B 5/06* (2013.01); *A61B 8/085* (2013.01); *A61B 8/5223* (2013.01); *G06T 5/002* (2013.01);
(Continued)

(58) Field of Classification Search
CPC .......... G09B 5/06; G09B 19/04; G09B 19/16; G06T 7/12; G06T 5/002; G06T 7/0012;
(Continued)

(56) References Cited

U.S. PATENT DOCUMENTS 8,696,577 B2    4/2014    Freiburger
8,825,492 B1*   9/2014    Buhadi ................. G09B 19/04
                                                        704/4

(Continued)

FOREIGN PATENT DOCUMENTS

WO    1999013446        3/1999
WO    2016122536 A1    8/2016

OTHER PUBLICATIONS

Preston et al., "Ultrasound Images of the Tongue: A Tutorial for Assessment and Remediation of Speech Sound Errors", Jan. 2017, Journal of Visualized Experiments, pp. 1-10 (Year: 2017).*

(Continued)

*Primary Examiner* — Pascal M Bui Pho
*Assistant Examiner* — Adil Partap S Virk
(74) *Attorney, Agent, or Firm* — Dinsmore & Shohl LLP

(57) ABSTRACT

Systems and methods for an enhanced ultrasound biofeedback therapy for an improved speech remediation treatment for an individual include transmitting a plurality of ultrasound (US) waves toward a tongue of the individual; receiving a plurality of reflected US waves; converting the plurality of reflected US waves into a plurality of US signals to transmit to an ultrasound machine; and generating one or more enhanced images of the tongue at least partially based (Continued)

on the US signals in real-time, the enhanced images including identified Regions of Interest (ROIs) along tongue sub-parts comprising the tongue root, the tongue dorsum, and the tongue blade and respective ROI points identified therein. An interactive visual story is generated and updated in real-time with a tongue-mapping trajectory of the individual on a display based on the enhanced one or more images to determine a successful or unsuccessful sound production.

19 Claims, 9 Drawing Sheets

(51) Int. Cl.
  *G06T 7/00* (2017.01)
  *G09B 19/04* (2006.01)
  *A61B 8/08* (2006.01)

(52) U.S. Cl.
  CPC ............ *G06T 7/0012* (2013.01); *G09B 19/04* (2013.01); *G06T 2207/10132* (2013.01); *G06T 2207/20104* (2013.01); *G06T 2207/30004* (2013.01)

(58) Field of Classification Search
  CPC .......... G06T 2207/10132; G06T 2207/20104; G06T 2207/30004; A61B 8/085; A61B 8/5223; A61B 8/469
  See application file for complete search history.

(56) References Cited

U.S. PATENT DOCUMENTS

| | | | |
|---|---|---|---|
| 2002/0103023 A1* | 8/2002 | Matsuura | A63F 13/60 463/31 |
| 2010/0312112 A1* | 12/2010 | Kamiyama | A61B 8/14 600/443 |
| 2012/0108973 A1* | 5/2012 | Osumi | A61B 8/0891 600/443 |
| 2013/0281856 A1* | 10/2013 | Freiburger | G16H 50/30 600/443 |
| 2014/0342324 A1* | 11/2014 | Ghovanloo | G09B 5/06 434/185 |

OTHER PUBLICATIONS

Sonosite, Titan System Specification, 2005 (Year: 2005).*
Wrench et al., "Very High Frame Rate Ultrasound Tongue Imaging", Jun. 1, 2011 (Year: 2011).*
Davidson, "Comparing tongue shapes from ultrasound imaging using smoothing spline analysis of variance", Jul. 2006, Journal Acoustic Society of America, pp. 407-415 (Year: 2006).*
Extended European Search Report pertaining to corresponding European Patent Application No. 18893005.1 dated Aug. 18, 2021.
Mozaffari, et al. "Guided Learning of Pronunciation by Visualizing Tongue Articulation in Ultrasound Image Sequences", 2018 IEEE International Conference on Computational Intelligence and Virtual Environments for Measurement Systems and Applications (CIVEMSA), 2018, 1-5.
Davidson "Comparing tongue shapes from ultrasound imaging using smoothing spline analysis of variance", The Journal of the Acoustical Society of America, 2006, 407-415, vol. 120 No. 1.
International Search Report and Written Opinion for PCT/US2018/067018 dated Mar. 22, 2019.
Jonathan L. Preston et al, Ultrasound Images of the Tongue: A Tutorial for Assessment and Remediation of Speec Sound Errors; Journal of Visualized Experiments, Jan. 2017, pp. 1-10.

* cited by examiner

SIMPLIFIED, INTERACTIVE, REAL-TIME ULTRASOUND BIOFEEDBACK SYSTEM FOR SPEECH REMEDIATION

CROSS-REFERENCE TO RELATED APPLICATIONS

This application is a national stage entry of and claims priority to International App. No. PCT/US2018/067018 (CIN0259WO), filed Dec. 21, 2018, entitled "SIMPLIFIED, INERACTIVE, REAL-TIME ULTRASOUND BIOFEEDBACK SYSTEM FOR SPEECH REMEDIATION," which claims the benefit of U.S. Provisional Application Ser. No. 62/609,356 (CIN0259MA), filed Dec. 22, 2017, entitled "Simplified, Interactive, Real-Time Ultrasound Biofeedback System for Speech Remediation," the entireties of which are incorporated by reference herein.

STATEMENT REGARDING FEDERALLY SPONSORED RESEARCH OR DEVELOPMENT

This invention was made with government support under DC0136681 and DC01731 awarded by the National Institutes of Health. The government has certain rights in the invention.

TECHNICAL FIELD

The present disclosure relates to an ultrasound-based system for speech therapy, and in particular to an enhanced ultrasound biofeedback therapy (UBT) system for an improved treatment of residual speech sound disorder (RSSD).

BACKGROUND

Speech remediation is often employed to help those with speech production disorders, which may include individuals attempting to learn correct pronunciation in a second language or other types of speech production disorders that are applicable to many children and adults. For example, RSSD is a speech production disorder that causes an inability to produce appropriate sounds, such as the /r/ sound (e.g., those affected producing "wabbit" for "rabbit"). UBT has provided for use of tongue imaging to assist with successfully training some of those with RSSD to produce sound correctly, such as the /r/ sound among other sounds including those in any language that involves a characteristic tongue shape. However, such successful training requires long periods of learning and extensive clinical resources to help those with RSSD, such as children, interpret the tongue imaging. Alternative systems and methods are desired for an improved treatment for those with RSSD.

BRIEF SUMMARY

According to the subject matter of the present disclosure, a system for an enhanced ultrasound biofeedback therapy for an improved speech remediation treatment for an individual through an improved user interface may include one or more processors, one or more memory modules communicatively coupled to the one or more processors, an ultrasound machine comprising a display and communicatively coupled to the one or more memory modules, a probe device communicatively coupled to the ultrasound machine, the probe device comprising a transducer, a user interface module communicatively coupled to the display of the ultrasound machine, the improved user interface of a computing device, or both, and machine readable instructions. The machine readable instructions may be stored in the one or more memory modules that cause the system to perform at least the following when executed by the one or more processors: transmit a plurality of ultrasound (US) waves from the probe device toward a tongue of the individual along a mid-sagittal plane from below a jaw area of the individual; receive, into the transducer of the probe device, a plurality of reflected US waves; convert, via the probe device, the plurality of reflected US waves into a plurality of US signals; transmit, via the probe device, the plurality of US signals to the ultrasound machine; and generate one or more enhanced images of the tongue at least partially based on the US signals in real-time, the enhanced images including identified Regions of Interest (ROIs) along tongue sub-parts comprising the tongue root, the tongue dorsum, and the tongue blade and respective ROI points identified therein.

In accordance with one embodiment of the present disclosure, a method for an enhanced ultrasound biofeedback therapy for an improved speech remediation treatment for an individual may include transmitting a plurality of ultrasound (US) waves from a probe device toward a tongue of the individual along a mid-sagittal plane from below a jaw area of the individual; receiving, into a transducer of the probe device, a plurality of reflected US waves; converting, via the probe device, the plurality of reflected US waves into a plurality of US signals; transmitting, via the probe device, the plurality of US signals to an ultrasound machine; and generating one or more enhanced images of the tongue at least partially based on the US signals in real-time, the enhanced images including identified Regions of Interest (ROIs) along tongue sub-parts comprising the tongue root, the tongue dorsum, and the tongue blade and respective ROI points identified therein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
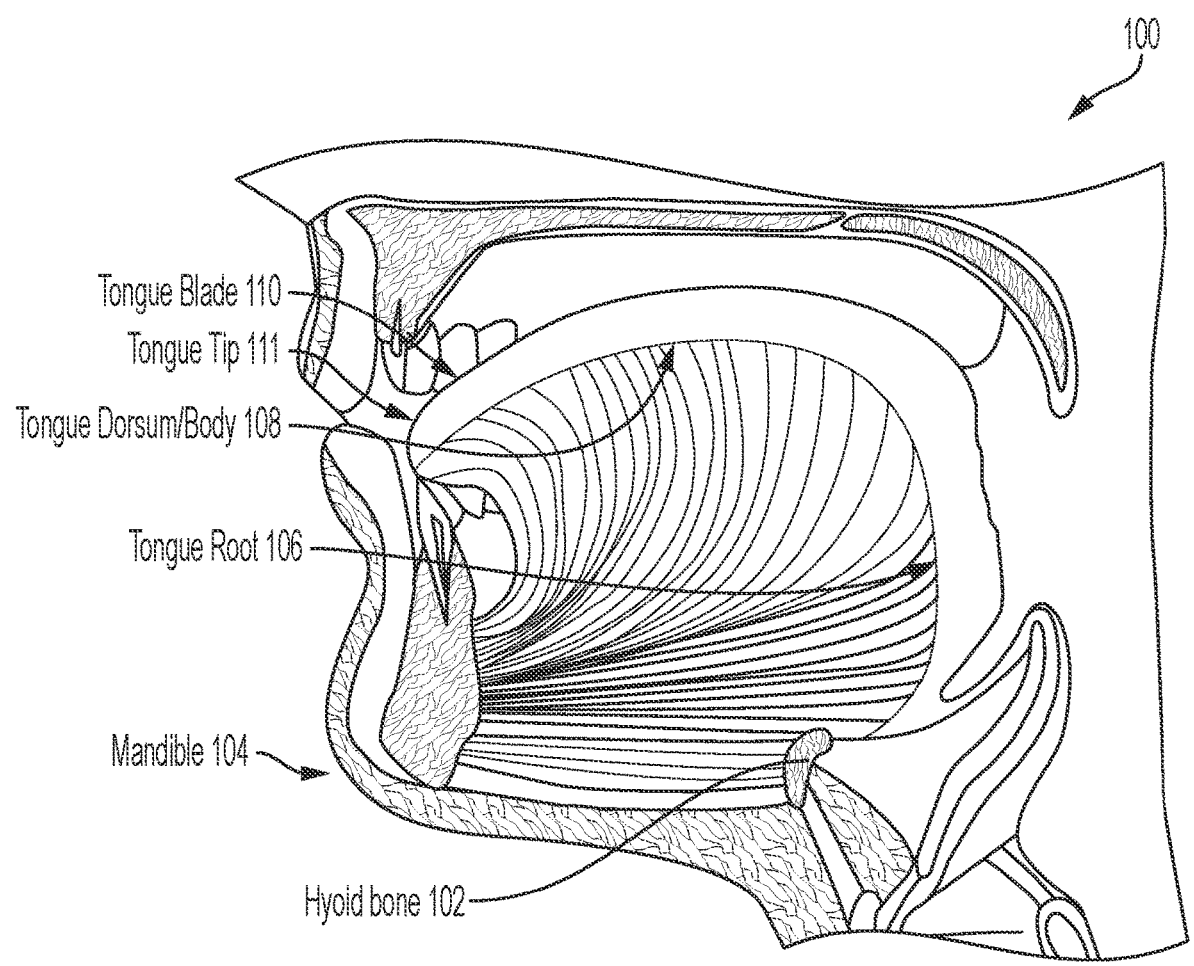
FIG. 1 schematically illustrates a side view of a tongue in a jaw of a person, according to one or more embodiments shown and described herein.

Referring initially to FIG. 1, a side view of jaw area 100 of a person along a sagittal plane includes a hyoid bone 102, mandible 104, and a tongue including a tongue root 106, a tongue dorsum (e.g., tongue body) 108, and a tongue blade 110 that ends at a tongue tip 111. A division between the tongue blade 110 and the tongue tip 111 may be determined by a function for speech. While the tongue tip 111 may be imaged, imaging interference may occur from a jaw shadow and from an air pocket under the tongue tip 111 during some speech sounds involving forward extension of the tongue tip 111. For the speech remediation systems and methods described herein, the ultrasound imaging, analysis, and enhancement within the scope of this disclosure focuses on imaging of the tongue blade 110 rather than the tongue tip 111. However, for speech remediation purposes, the tongue blade 110 and the tongue tip 111 may be considered as moving together.

Ultrasound technology is able to create an ultrasound image of the tongue, such as when an ultrasound probe is placed under the jaw of a person to generate a real-time ultrasound image for display. Such a real-time ultrasound image may be used to teach those with Residual Sound Speech Disorders (RSSD) issues, including children, that have difficult correctly producing sounds due to improper tongue placements to produce correct tongue shapes. However, ultrasound imaging of tongue shapes may be complex to interpret for a clinician and/or an individual with RSSD, particularly if they are a child, and progress toward articulatory accuracy may be difficult to achieve.

By way of example and not as a limitation, an ultrasound machine may include a display, and a probe device including a transducer is communicatively coupled to the ultrasound machine for ultrasound imaging generation. Ultrasound transducers coupled to the ultrasound machine may emit ultrasonic pulses from, for example, a 128 element array in a non-ionizing manner toward a bodily substance and collect sound waves that bounce and are reflected back to create and display images on the ultrasound machine. The ultrasound transducer may record changes in amplitude and direction of the reflected acoustic waves to measure and display these waves as a real-time image through conversion of the reflected waves into ultrasound signals to send to the ultrasound machine.

The methods described herein are directed to the successful effect resulting from proper tongue placement rather than training an individual through focus on such proper tongue placement. Thus, the methods enhance sensorimotor learning of the individual with RSSD through a simplified ultrasound feedback mechanism that employs an externally-directed attentional focus through an interactive visual story as a gamified approach. Such an approach assists to advance treatment of RSSD by quantifying complex tongue movements captured by ultrasound into trajectories and transforming those trajectories into simplified, real-time, interactive, and customizable feedback to drive tongue movements toward goal movement patterns.

Figure 2:
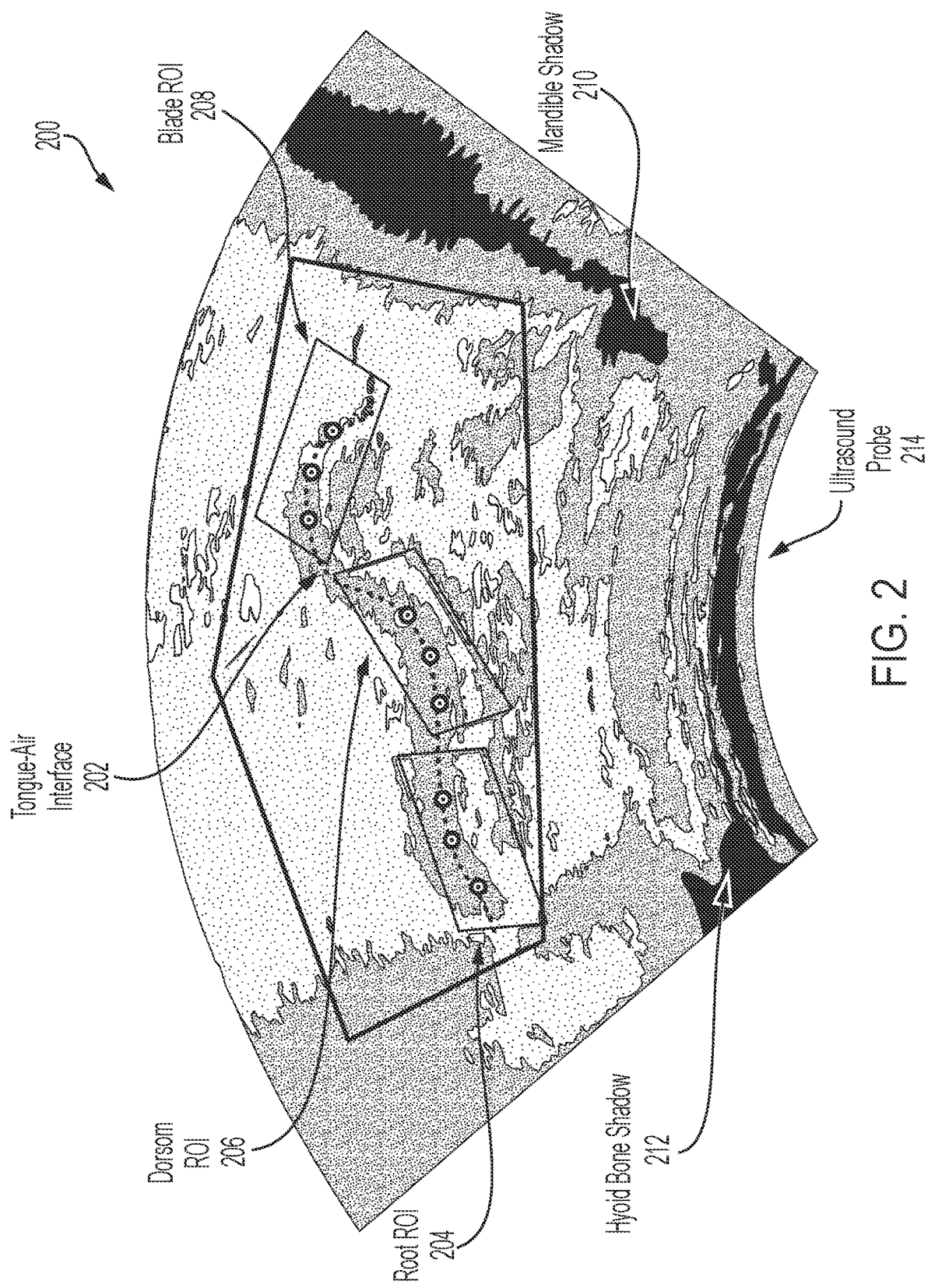
FIG. 2 is an example ultrasound view of the tongue of a person including identified Regions of Interest (ROIs) along a tongue-air interface, according to one or more embodiments shown and described herein.

The tongue-mapping approach described herein may be implemented through an ultrasound component 1312 and a tongue-mapping component 1316 as described in greater detail with respect to the system 1300 further below. The tongue-mapping approach is directed to identifying and placing a Region of Interest (ROI) around a midsagittal plane of the tongue in an ultrasound image frame, such as along a vowel midpoint as shown in FIG. 2. In the embodiment of FIG. 2, an ultrasound image 200 of a tongue of a person includes identified Regions of Interest (ROIs) along a tongue-air interface 202. The ROIs include a Root ROI 204, a Dorsum ROI 206, and a Blade ROI 208. The ultrasound image 200 further illustrates a mandible shadow 210, a hyoid bone shadow 212, and an area of positioning of an ultrasound probe 214 under the jaw of the person to create the ultrasound image 200. The method includes detecting the hyoid and jaw shadows and detecting the tongue-air interface 202 appearing as a bright curve between these shadows. The identified ROIs along the mid-sagittal tongue-air interface 202 may then be automatically detected and assigned, corresponding to the tongue blade as the anterior tongue contour portion, the dorsum as the median tongue contour portion, and the tongue root as the posterior tongue contour portion. For example, the method further may include pre-processing of the ultrasound image with the identified ROIs such as by blurring or otherwise filtering the image (e.g., using a Hann Window technique in an embodiment), identification of local brightness indicia to identify the tongue-user interface, and automatic assignment of the tongue regions (root, dorsum, blade) along with at least one reference point in each tongue region along the tongue-user interface. In an embodiment, the automatic assignment of the tongue regions (root, dorsum, blade) may include three reference points in each tongue region along the tongue-user interface. The method may determine a nominal tongue length based on middle reference points along the blade and root of the tongue and normalize displacements of each sub-part through division by the nominal tongue length.

In an embodiment, instead of identifying one or more ROIs of the tongue, the tongue itself may be identified from an image such that a calibration point may be used to (1) describe a gain-adjustment function, which begins darkening the image below this calibration point; and 2) select a first point on the tongue as the local maxima with the shortest Euclidean distance from this calibration point. A threshold may be based on a mean brightness of the image. Use of tongue points from a previous frame may be used as an estimate for a bulk of the points on a next frame by applying a search window to them. The anterior and posterior directions may further be searched for any additional points identifying the tongue.

Sections of repetitive code may be placed into sub-functions for ease of change to the sub-functions rather than changing a larger GUI script. The arrays that store the tongue points and displacements may further include every production at once to permit views of multiple productions from within the GUI without needing to re-run each production. For example, after selecting a "Run All" feature, a viewer may be able to review any frame of any production, and the corresponding displacement plot, without needing to run the production again. This permits the storage of a single .txt file containing all of the displacements and x/y coordinates for every production of a speaker, as well as similarly organized .mat files to assist with data analysis significantly.

Figure 3:
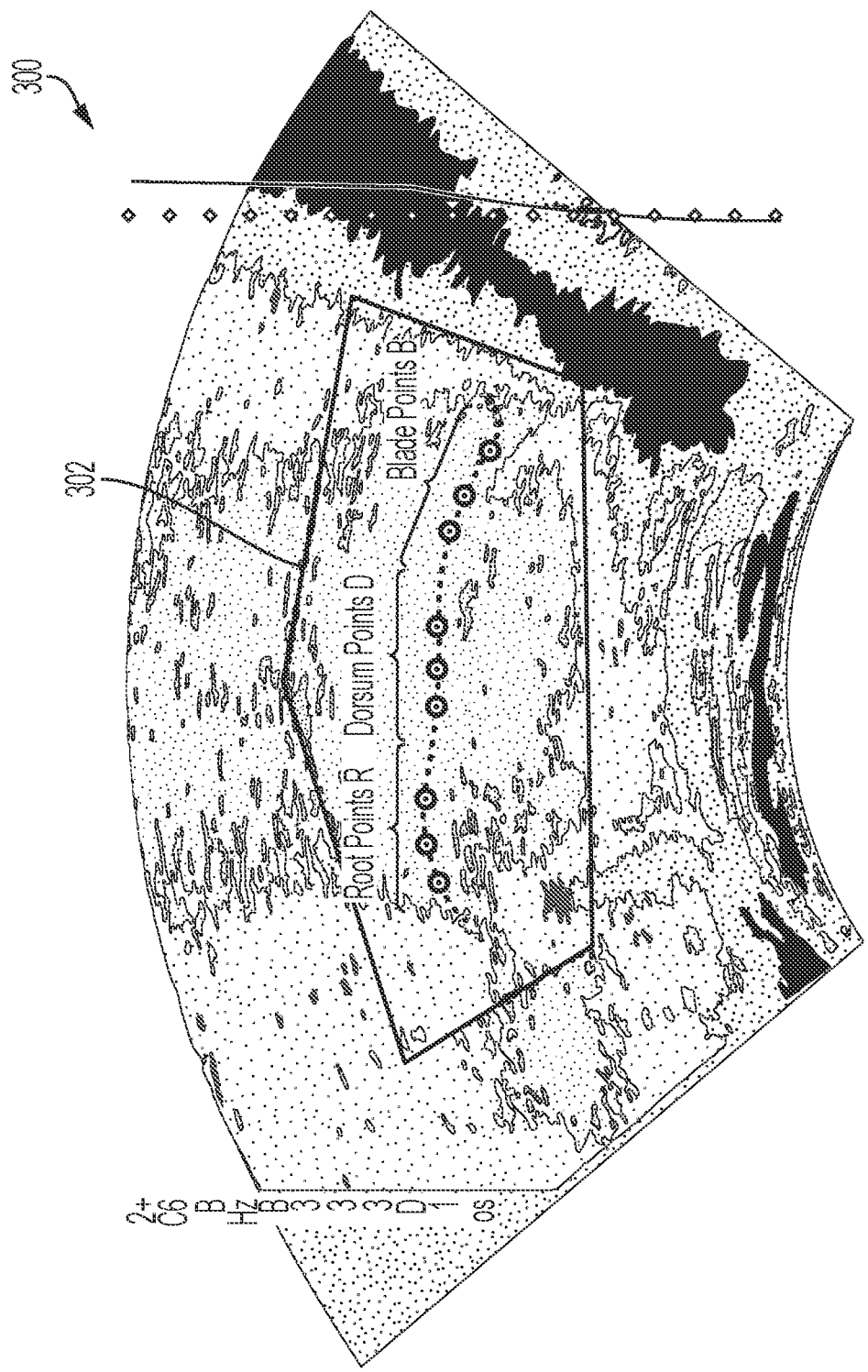
FIG. 3 is another example ultrasound view of the tongue of a person including identified points in one or more ROIs along the tongue-air interface (e.g., identified ROI points) along the tongue-air interface, according to one or more embodiments shown and described herein.

Referring again to the tongue-mapping approach, FIG. 3 illustrates an ultrasound image 300 of a tongue of a person including identified ROI points disposed along the tongue-air interface (shown as tongue-air interface 202 in FIG. 2) captured within a ROI 302. The ROI points include Root Points R, Dorsum Points D, and Blade Points B. The method includes a tongue-tracking algorithm such that, when the tongue moves, normalized displacements of each region from a starting position (e.g., an acoustic midpoint of an /a/ sound) are calculated. Displacement trajectories for each region (e.g., from the midpoint of the /a/ sound to an end of the /r/ sound) may then be resampled and interpolated to a specific length. It is contemplated within the scope of this disclosure that sounds may be analyzed in this manner and with any of the systems and methods described herein beyond the /ad sound, including one or more sounds in any world language that involves a characteristic tongue shape. It is to be understood that the phonetic notation /a/ as set forth herein is representative of a vowel sound in "ah" or "pot," and that the phonetic notation /r/ as set forth herein is representative of an initial sound in "rot" or the final sound in "her." Representative average trajectories of tongue parts for those with RSSD and those that are typically-developing (TD) may then be generated and compared. A root-mean-square (RMS) displacement of the tongue may be computed over the root, dorsum, and blade tongue portions for all temporal sample points in all productions. The RMS values are representative of an overall magnitude of motion for each individual during an /ar/ articulation.

Through an analysis of a group of children with RSSD and children with TD, results found that a child with RSSD has a lower range of RMS values indicative of a lower magnitude of motion than a TD child without RSSD such that the TD child produces an /ar/ sound without difficulty. An average RMS displacement in the analysis was found to be 0.1158 (+/−0.0451) for TD children and 0.0731 (+/−0.0262) for RSSD children. Further, overall tongue motion was found to be significantly greater for the TD group than the RSSD group. Thus, a child with RSSD thus is found to exhibit a smaller magnitude of tongue part movement during /ar/production than a TD child. Root and dorsum trajectories were highly positively correlated for /ar/ production in TD children but were not highly correlated in RSSD children. Blade and dorsum trajectories were negatively correlated in TD children and, in contrast, positively correlated for /ar/ production in RSSD children. The feedback system described herein is configured to input such results, analysis, and trajectories of correct and incorrect sound productions to promote tongue part differentiation and train an individual to produce correct sound productions. The RMS values are able to be provided as input into the feedback system to quantify differentiation of tongue parts and identify magnitude of tongue production leading to such correct and incorrect sound productions.

Figure 4:
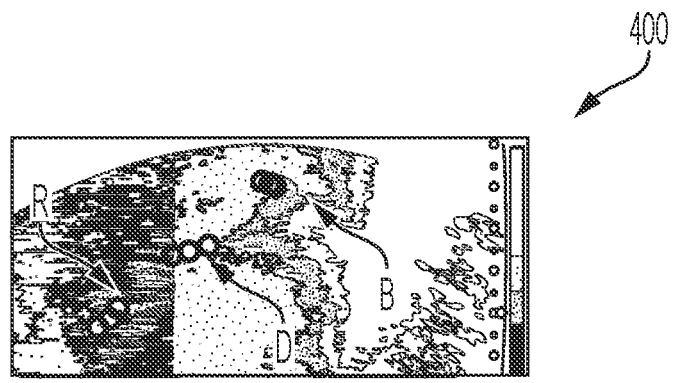
FIG. 4 is an example ultrasound view of identified ROI points as reference points along a tongue-air interface of a person forming an /a/ sound, according to one or more embodiments shown and described herein.
Figure 5:
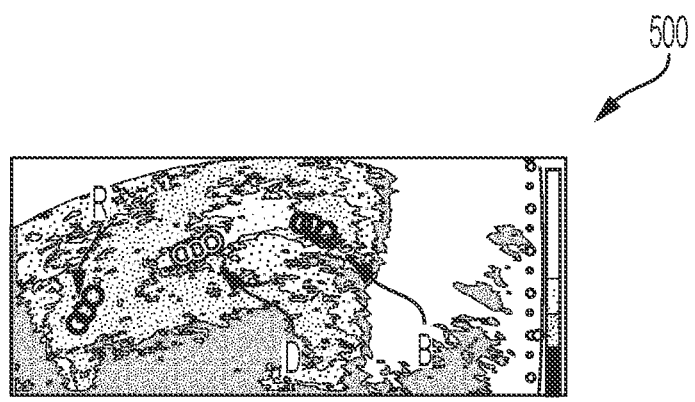
FIG. 5 is an example ultrasound view of identified ROI points as reference points along a tongue-air interface of a person forming an /r/ sound, according to one or more embodiments shown and described herein.

FIG. 4 illustrates an ultrasound image 400 of identified ROI points as reference points Root Points R, Dorsum Points D, and Blade Points B along a tongue-air interface of a person forming an /a/ sound. To arrive at the ultrasound image 400, three ROIs identified through the method as described herein may be placed along the mid-sagittal tongue-air interface contour in the /r/ frame, after which image frames are smoothed by a two-dimensional convolution with a 48×48 pixel (8.8×8.8 mm$^2$) kernel constructed by multiplying Hann windows (raised cosine functions) along horizontal and vertical directions. It is to be understood that other forms of a filter kernel are within the scope of this disclosure. In an embodiment, smoothing may occur through use of a low-pass filter. Next, local brightness maxima within each ROI may be identified, where the brightest points within these ROIs occurring at the tongue-air interface such that the local brightness maxima of the ultrasound image analyzed provides a reliable tongue position estimate. The system may dispose the respective ROI points in each identified ROI along the local brightness maxima representative of the tongue-air interface. The ultrasound image may then display the detected local brightness maxima of a low-pass filtered /a/ sound production frame within each ROI, and reference points in the ROIs as R, D, and B are able to be displayed in the ultrasound image 400 for image from an acoustic midpoint of the /a/sound production. FIG. 5 illustrates an ultrasound image 500 of identified ROI points as reference points along a tongue-air interface of a person forming an /r/ sound. The ultrasound image 500 is created similar to how the ultrasound image 400 is created yet with respect to a In sound production. Thus, reference points in the ROIs as R, D, and B are able to be displayed in the ultrasound image 500 for image from an acoustic midpoint of the /r/ sound production.

A position of maximum pixel brightness may be determined for each vertical image segment (e.g., column of a grayscale data matrix) that falls within the blade and dorsum ROIs. Further, local maxima with brightness values below a threshold may be discarded, such as a brightness values less than 60% of an overall brightness maximum. The coordinates of remaining local maxima for each ROI comprise an ordered vector from left to right (posterior to anterior) with a length N. Three internal reference points for each ROI may then be defined, such as the coordinates with indices closest to N/3, N/2, and 2N/3 along the ordered vector. Relative displacements may then be calculated through computing a mean difference in a vertical position of these three reference points in pixel based units between an /a/ frame (FIG. 4) and an /r/ frame (FIG. 5), with positive displacement defined as an increase in vertical position from /a/ to /r/ corresponding to a constriction of a vocal tract.

The same procedure may be applied to the root ROI except that local brightness is tracked along a leading diagonal axis extending from anterior to posterior and inferior to superior based on preliminary data identifying these axes as primary dimensions of tongue part variations. Dimensional measures of tongue part displacements may be obtained by normalization of the relative displacements for each ROI by a reference distance, which is defined as a distance between midpoints of the blade and root ROIs computed in pixel-based units. The reference distance is approximately proportional to a tongue length such that the normalized displacement of each tongue part is defined as a dimensionless ratio of each part's measured displacement to the reference distance.

Figure 6:
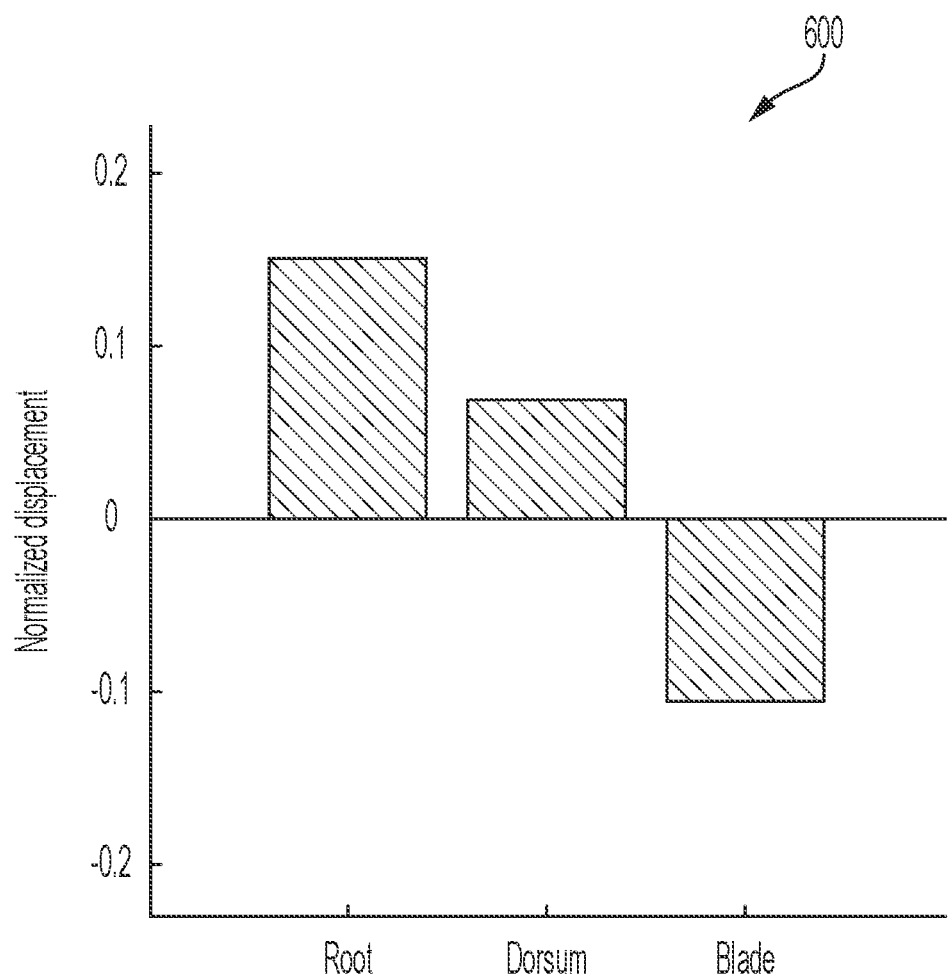
FIG. 6 is a graphical illustration of normalized tongue displacements of the root, dorsum, and blade calculated from displacement differences between the reference points shown in FIGS. 4-5.

FIG. 6 illustrates a graph 600 of normalized tongue displacements of the root, dorsum, and blade calculated from displacement differences between the reference points shown in FIGS. 4-5. In particular, FIG. 6 shows normalized displacements measured from the /a/ frame to the /r/ frame for sound production between the /a/ sound of FIG. 4 and the /r/ sound of FIG. 5. FIG. 6 illustrates that detected tongue motion with respect to this sound production includes a negative displacement of the blade of the tongue, a slight positive displacement of the dorsum of the tongue, and a larger positive displacement of the root of the tongue. This is indicative of the blade moving in the inferior direction, the dorsum moving slightly in the superior direction, and the root moving in the superior/posterior direction. Thus, for the sound production between the /a/ sound of FIG. 4 and the /r/ sound of FIG. 5, the vocal tract is constricted at the root position, slightly constricted at the dorsum position, and expanded at the blade position of the tongue.

The approach to measuring tongue part displacement as described herein is configured for use with the real-time tracking of tongue motion as described herein. Thus, for ultrasound image data recorded as digital videos, tongue part displacements from individual frames are able to be tracked relative to a static reference frame using the same ROI per frame and at rates such as greater than 30 frames per second (fps). Once ROIs are identified on the static reference frame, the same ROIs may be automatically placed in the same position on each subsequent frame. The method of measurement of tongue displacements as described herein is configured to be incorporated into real-time ultrasound biofeedback therapy systems to enhance such systems with a tongue-tracking methodology to assist a user with reaching a target tongue displacement, such as through an interactive visual display as described in greater detail below with respect to FIGS. 12A-12E.

Figure 7:
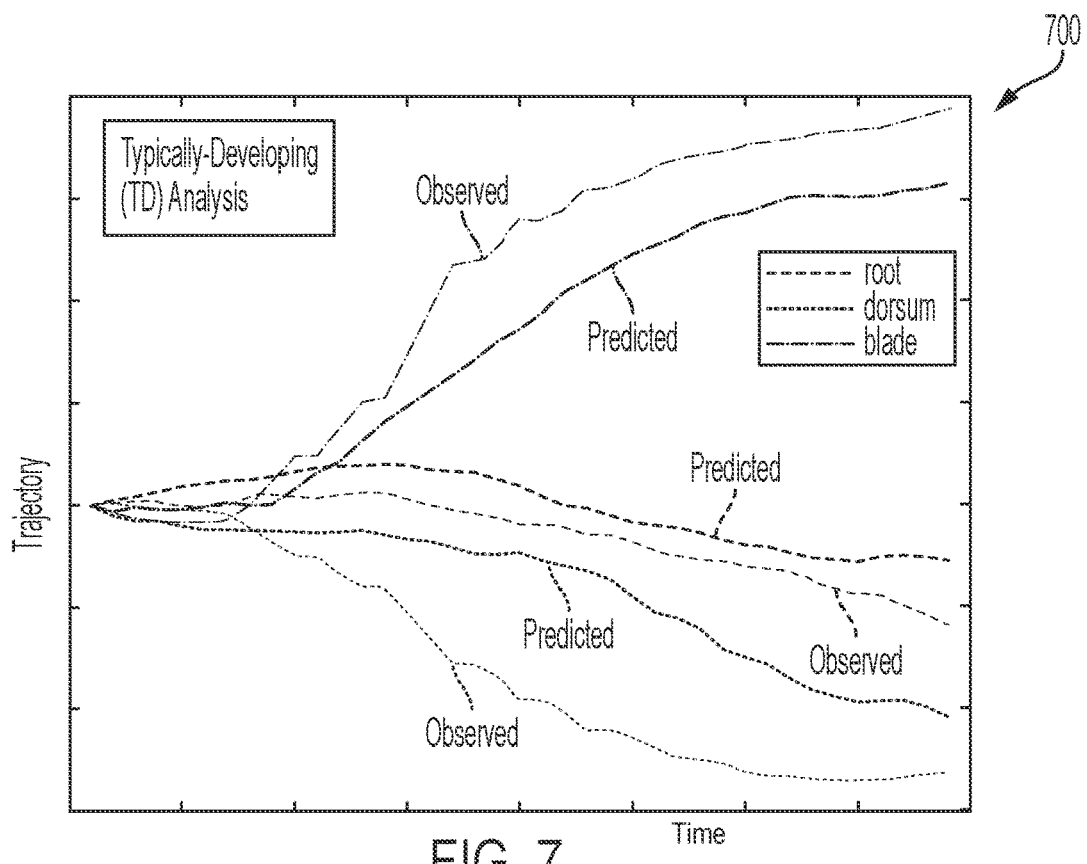
FIG. 7 is a graphical illustration of observed and predicted tongue portion trajectories for Typically-Developing (TD) children using a Principle Component Model (PCM) analysis from children with Residual Speech Sound Disorders (RSSD), showing non-similar trajectories between the PCM-predictor model and the TD trajectory.
Figure 8:
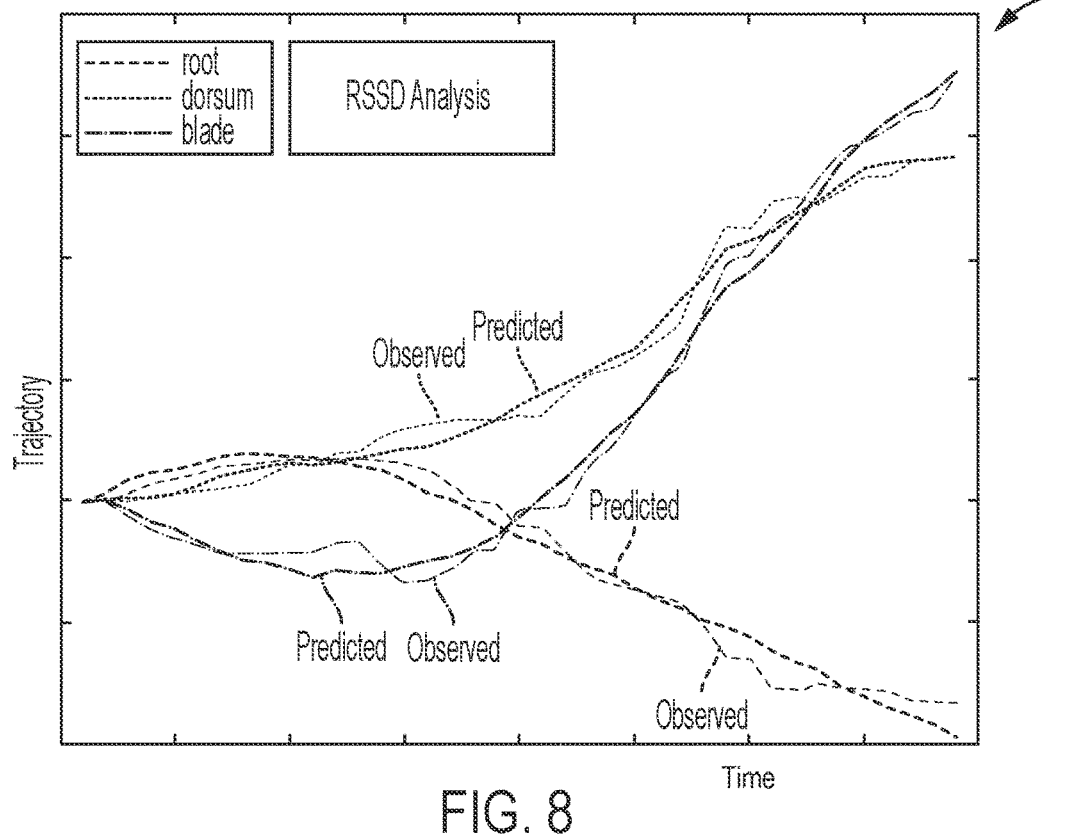
FIG. 8 is a graphical illustration of observed and predicted tongue portion trajectories for RSSD children using a PCM analysis from children with RSSD, showing similar trajectories between the PCM-predictor model and the RSSD trajectory.

FIGS. 7-8 illustrate another analysis of correct versus incorrect tongue displacement, yet against two groups of children through a Principal Component Model (PCM) analysis. The PCM analysis is configured to identify an optimal number of components associated with a majority of variance in the analyzed data set and consists of a transformation of original variables into new uncorrelated Principal Components Z. The PCM is Z=U'*X, where columns of U are loading vectors of a matrix X including original data.

For example, FIG. 7 illustrates a graph 700 of observed and predicted tongue portion trajectories for Typically-Developing (TD) children using a PCM analysis from children with Residual Sound Speech Disorders (RSSD), showing non-similar trajectories between the PCM-predictor model and the TD trajectory. FIG. 8 illustrates a graph 800 of observed and predicted tongue portion trajectories for RSSD children using a PCM analysis from children with RSSD, showing similar trajectories between the PCM-predictor model and the RSSD trajectory. Thus, observed and predicted trajectories from the PCM analysis illustrate that the PCM from the RSSD group is similar to a trajectory from a child with RSSD, but the PCM-predictor model does not match a TD trajectory of a child without RSSD. Furthermore, FIGS. 7-8 assist with determining improper and proper tongue displacements for sound production. For example, children with TD trajectory have greater range of motion and tongue displacement than children with RSSD trajectory.

Figure 9:
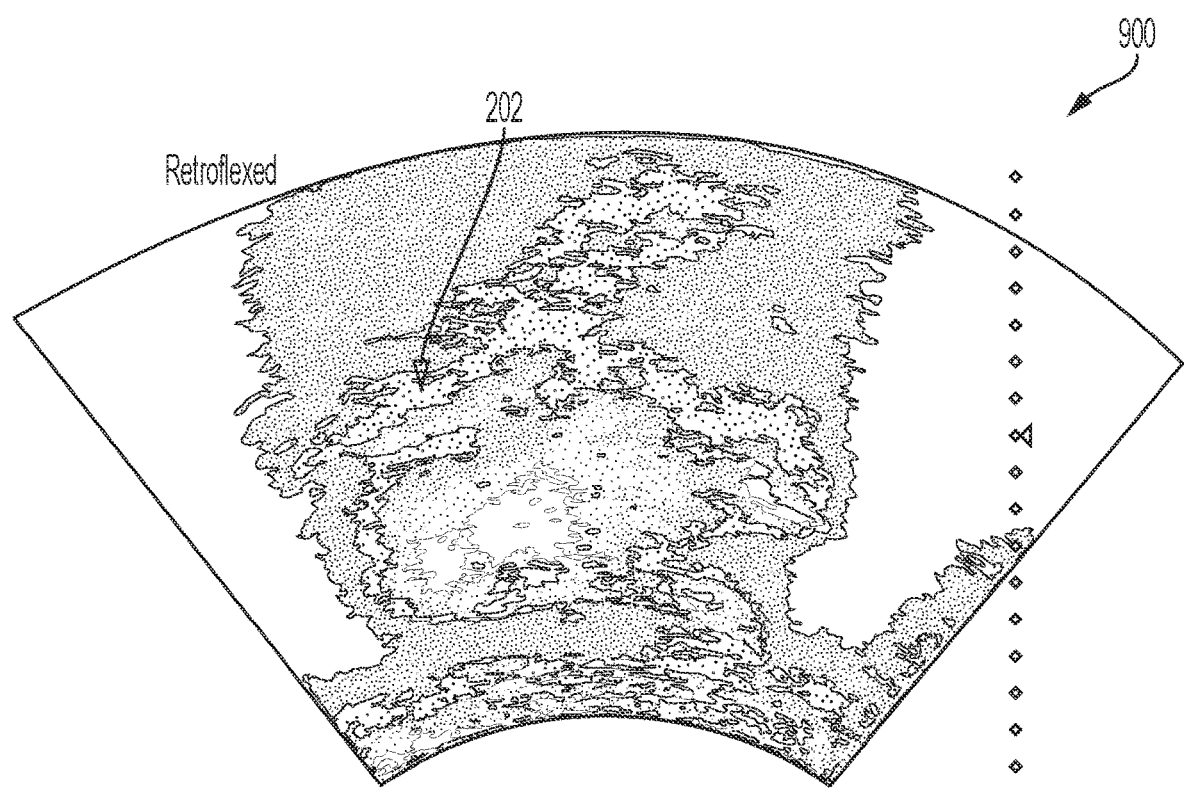
FIG. 9 is an example ultrasound view of a retroflexed tongue shape of a person, according to one or more embodiments shown and described herein.
Figure 10:
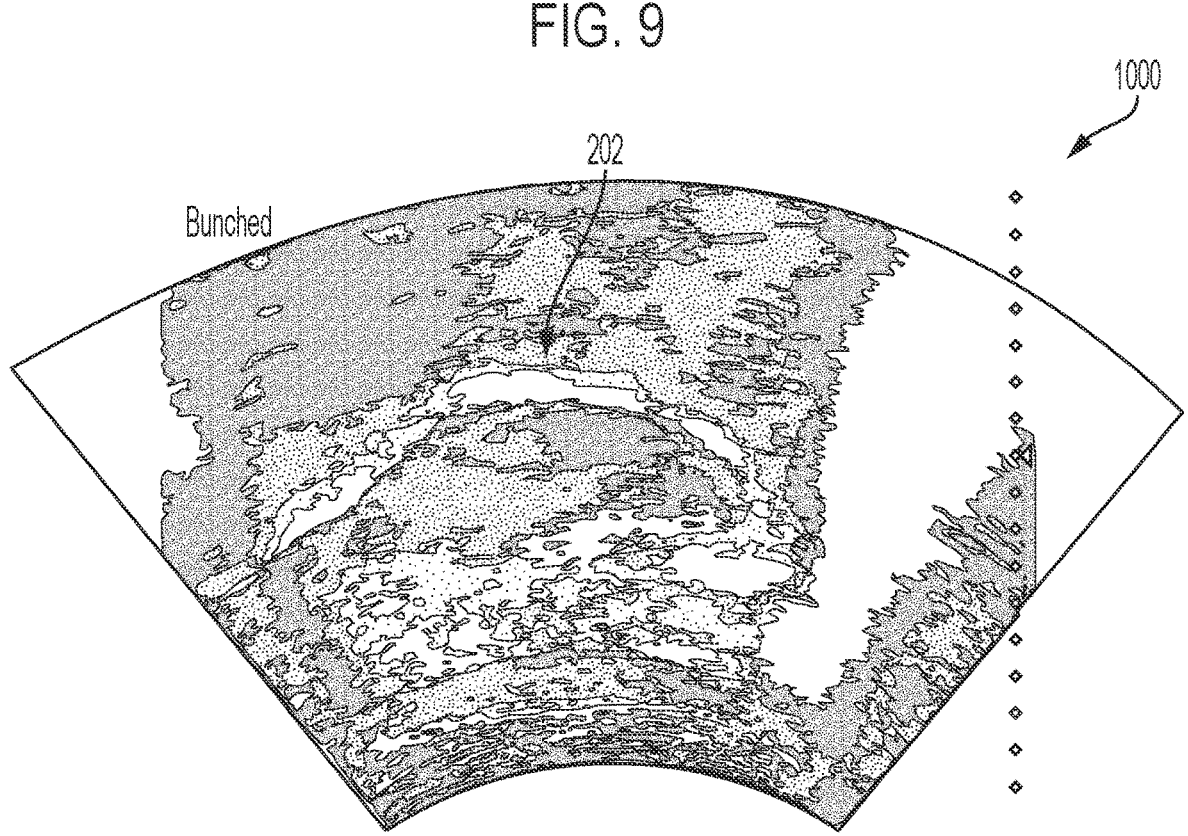
FIG. 10 is an example ultrasound view of a bunched tongue shape of a person, according to one or more embodiments shown and described herein.
Figure 11:
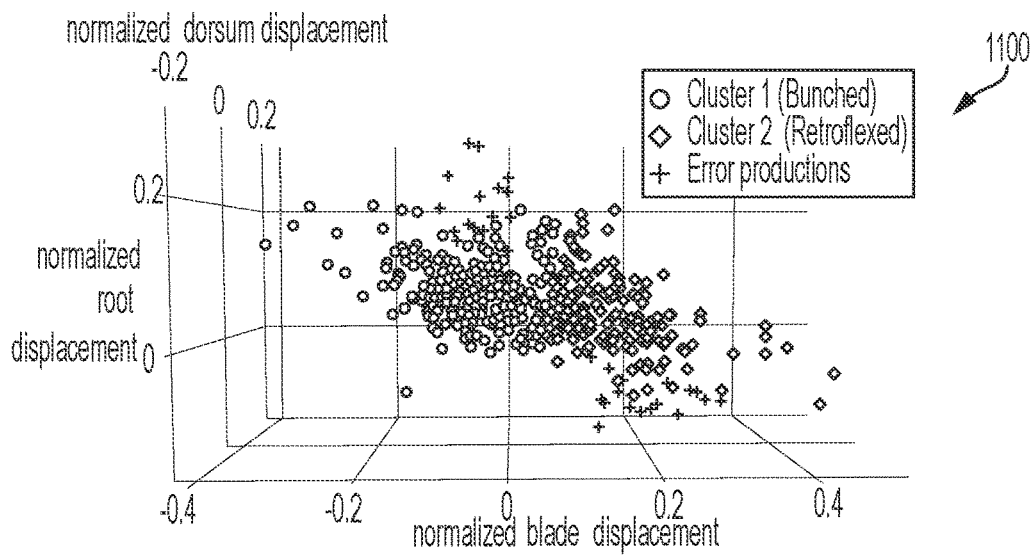
FIG. 11 is a graphical illustration of a cluster analysis of tongue movements for a first cluster associated with bunched tongue shapes and a second cluster associated with retroflexed tongue shapes, each point representative of a produced /ar/ sound by a person along with illustrated error productions of the /ar/ sound, according to one or more embodiments shown and described herein.

In another embodiment, a cluster analysis may be conducted to assist with a goal of automatically identifying accurate tongue movements for a sound or group of sounds, such as the /ad syllable. Multiple tongue shapes can actually product the correct sound, such as an acceptable In, and a cluster analysis may assist with identification of correct tongue patterns of tongue part displacements for correct sound productions, such as correct /ar/ syllable. FIGS. 9-11 are presented to illustrate and explain such a cluster analysis.

FIG. 9 illustrates an ultrasound image 900 of a retroflexed tongue shape of a person. FIG. 10 illustrates an ultrasound image 1000 of a bunched tongue shape of a person. FIG. 11 illustrates a graph 1100 of a cluster analysis of tongue movements for a first cluster associated with bunched tongue shapes (as shown in FIG. 10) shown as circles and a second cluster associated with retroflexed tongue shapes (as shown in FIG. 9) shown as diamonds. Each point is representative of a produced /ad sound by a person. Further illustrated are error productions of the /ad sound shown as crosses. The clusters shown are observations of displacements from the acoustic midpoint of /a/ to the acoustic midpoint of In, which observations share characteristics with each other, yet are dissimilar to observations belonging to other clusters, and are compared against a data set of normalized tongue displacements for the root, dorsum, and blade.

Results of the cluster analysis shown in FIG. 11 illustrate characteristics of two clusters of typical adult articulatory data. The two clusters include a first cluster as Cluster 1 for a bunched tongue shape of FIG. 10 and a second cluster as Cluster 2 for a retroflexed tongue shape of FIG. 9. The 3D scatterplot of FIG. 11 of the typical adult articulatory data mapping out blade, root, and dorsum displacements illustrates correct Cluster 1 productions as circles and correct Cluster 2 productions as diamonds to show the spread of observations within the sampled data set. The adjacent two correct clusters with minimal overlap is indicative of displacements characteristics of perceptually correct /ar/ sound articulation does not partition into distinct, discrete categories but is more continuous between the clusters.

Error sound productions are shown as crosses in FIG. 11. In particular, the crosses are representative of /ar/ production data from two adults with residual /r/ errors overlaid on the typical adult data cluster 3D scatterplot. Unlike the correct cluster displacements, the error productions are indicative of movement in discontinuous, discoordinated, undifferentiated ways.

In an embodiment of conducting a cluster analysis, a statistical analysis software such as R (Version 3.3.1) may be used for a cluster analysis to determine an optional number of cluster for a data set. For example, a 2-cluster analysis may be determined to be the optimal number of clusters for the data set based on an NbClust package, using a squared Euclidean distance measure of dissimilarity, complete linkage, a k-means iterative partitioning method, and the cubic clustering criterion to select the number of clusters. Squared Euclidean distance may be chosen as the dissimilarity measure due to its propensity to reduce the importance of small distances and increase the importance of larger distances.

The enhanced ultrasound biofeedback therapy (UBT) system for an improved treatment of residual speech sound disorder (RSSD) described herein may incorporate the tongue-mapping algorithms as described herein to provide enhanced ultrasound imaging including identified ROI points as defined herein include Root Points R, Dorsum Points D, and Blade Points B. Such identified ROI points and tongue displacement data to identify correct versus incorrect tongue displacements and to track tongue displacements real-time for a user may be utilized in a gamified approach to encourage a user to focus on a goal of correct tongue displacement rather than focuses on reading an ultrasound image to correct a respective tongue displacement.

The enhanced UBT system described herein is configured to utilize ultrasound technology to track relative displacements of the tongue, including the blade, dorsum, and root, in real-time with a low latency, such as under 0.1 seconds, for speech sequences such as /ar/ and /ir/ sound productions while providing an automatic evaluation of correct and incorrect productions using the real-time measures and imaging. The enhanced UBT system is configured to identify consistent patterns distinguishing correct versus incorrect sound production of specific speech sequences and automatically track motion of tongue part of a user of the system in real time through the enhanced ultrasound imaging described herein with the identified, overlaid ROI points for each tongue part. The enhanced UBT system is configured to identify effective biofeedback targets through, for example, a cluster analysis approach to identify one or more tongue motion patterns for correct sound production, such as for /r/ and /l/ sound production.

The enhanced UBT system is further configured to map measured tongue displacements onto an interactive visual display, such as the one shown in FIGS. 12A-12E, to allow users to control feedback through their tongue motion tracked in real-time. The biofeedback may be gamified through using a customizable visual-story interface based on the enhanced ultrasound imaging to increase motivation and adherence to the training of the user. The enhanced UBT system is based on identifying correct versus incorrect productions as described herein on the interactive visual display in real-time while tracking tongue part differentiation. Such tongue part differentiation is representative of an ability of an individual to move a tongue root and a tongue front portion (including the dorsum and blade) in different directions simultaneously. The tongue surface curves are reduced from grayscale ultrasound images to point-motion data to summarize the relative motion of each tongue part as described herein. Further, tongue motion capture data is configured to track local brightness maxima as described herein with ROIs corresponding with tongue parts, such as the root, dorsum, and blade as described herein. The enhanced UBT system is configured to focus on and track such tongue parts separately as independent elements along the tongue-air interface for displacement comparison with respect to one another and to perform a real-time analysis as described herein of user tongue movement while producing a particular sound. The methodology applied herein is directed to detection of brightness maxima in a grayscale ultrasound image with the enhanced ultrasound imaging, such as along the tongue-air interface, to track tongue motion in a more accurate, efficient, and speedy process.

Figure 12A:
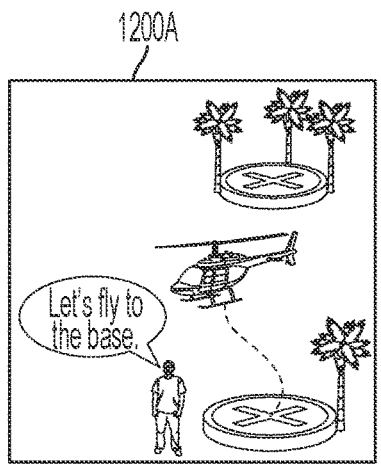
FIG. 12A is a schematic illustration of a graphical user interface (GUI) display of an instruction screen of an interactive visual story, according to one or more embodiments shown and described herein.

The enhanced ultrasound imaging as described herein may further be utilized with an interactive visual story through, for example, a gamified approach. By way of example, and not as a limitation, FIG. 12A illustrates an instruction screen 1200A of such an interactive visual story. When gamified, the GUI is provided through the interactive visual story that provides users with a goal to achieve along with a score for each sound production and a running total score. As a user improves toward achieving the goal of success sound production for particular sound sequences, the user may advance to start the game at a higher, more difficult level to increase the challenge of achieving the goal. A higher level goal is achieved, for example, by making the gains determined by the biofeedback system that map tongue displacements to the feedback display more increasingly sensitive (e.g., decreased) such that smaller tongue displacements create larger displacements of the graphical object.

The enhanced UBT system is thus configured to map tongue part displacements onto a GUI display that moves in real-time in response to detected tongue part motion through the enhanced ultrasound imaging technology described herein utilized with a user. The users are presented with a visual goal rendered as a visual story, such as the one shown in FIG. 12A, rather than, for example, real-time ultrasound imaging of the user's tongue. Tongue part displacements associated with a successful production of a sound sequence will move a graphical object (e.g., a helicopter) on the GUI display uniformly along a trajectory from a start location (e.g., of the helicopter) to a goal location (e.g., the island base) on the GUI display. The system is configured to determine a successful sound production when the tongue-mapping trajectory comprising a multi-part trajectory of the tongue sub-parts matches a desired path comprising one or more defined targets, where the desired path is configured for display on the interactive visual story. Alternatively, tongue part displacements associated with an unsuccessful production of a sound sequence will cause the graphical object to deviate from the goal with a magnitude and direction that is proportional to an error in tongue movement. The system is configured to determine an unsuccessful sound production when the tongue-mapping trajectory fails to match the desired path on the interactive visual story.

The GUI display may be based on an invariant underlying engine implemented in computer programming code, such as C++ and OpenGL, to computer displayed trajectories on the GUI display. The displayed trajectories are based on tongue part displacements measured by automatic image tracking methods and feedback parameters as described herein. Such parameters may include gain, an error factor, threshold, and proportional influence biofeedback parameters. The gain is representative of an amplitude associated with tongue part movements to the amount of visual motion on the feedback display. The error factor is indicative of a coefficient to determine the magnitude of deviations of the graphical feedback object in response to erroneous tongue part movements. Adjustment of this parameter may adjust respective criteria for accuracy by increasing or decreasing such criteria. The threshold of tongue part displacement is a magnitude that yields a change in the feedback display. The proportional influence (e.g., weight) of tongue part movements (e.g., for /r/ and /l/ sound productions) may be determined based on the movement in the biofeedback display. The engine may be configured to permit adjustment to display settings (e.g., selection of a type of visual story) and the feedback parameters by, for example, a clinician. The engine is further configured to receive as input streaming, dimensionless tongue part displacements recorded per each video frame and map the displacements to screen coordinates for a feedback graphical object.

Figure 12B:
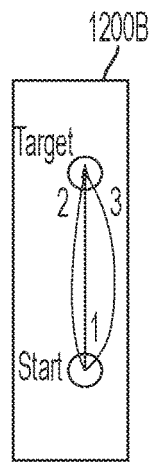
FIG. 12B is a schematic illustration of a GUI display of three example correct productions for the interactive visual story, according to one or more embodiments shown and described herein.
Figure 12C:
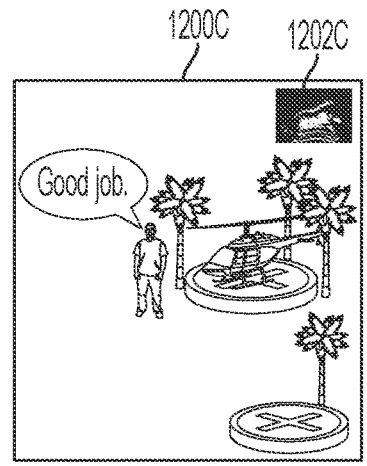
FIG. 12C is a schematic illustration of a GUI display of a successful production screen of the interactive visual story, according to one or more embodiments shown and described herein.

As a non-limiting example of a successful production of a sound sequence per the interactive visual story, FIGS. 12B-12C display screens respectively showing a variety of potentially successful tongue displacements to arrive at the goal location and a successful production resulting in reaching the goal location. FIG. 12B illustrates a correct productions mapping screen 1200B showing three example correct productions of tongue placement to achieve success for the interactive visual story of FIG. 12A. The possible correct productions may be computed by mapping tongue sub-part displacements to screen coordinates. FIG. 12C illustrates successful production screen 1200C indicative of a success of a user in reaching the target in the interactive visual story through a production of correct tongue placement. A successful production may result in a pilot appearing on the successful production screen 1200C with encouraging feedback for the user. An ultrasound image 1202C of the successful tongue production may be visible on a display presented to, for example, a clinician.

In an embodiment, a successful strategy for moving between /a/ and /r/ is to move the tongue root superiorly and posteriorly, the tongue dorsum superiorly by about half the tongue root displacement, and the tongue blade inferiorly by about two-thirds the tongue root displacement, which corresponds with a bunched tongue shape for the /r/ sound. A user producing these proportional displacements for the /r/ sound should be able to move the feedback graphical object successfully along a desired line on the GUI display to arrive at the successful production screen 1200C. In embodiments, the desired line associated with a sound may be a predetermined line such as a straight line or other desired path to follow based on one or more predetermined tongue displacements stored in the system as successful tongue displacements for the sound. The displacement factor may be determined by multiplying a gain factor by a summed relative displacements of tongue parts as mapped to pixel coordinates. However, movement of the tongue parts in an undifferentiated or otherwise incorrect differentiated manner will cause the trajectory of the graphical object to laterally deviate from the successful path by error factor representative of an amount proportional to the discrepancy between expected and actual tongue part displacements. Thus, if all sub-part displacements are correct relative to one another but are less or greater than the required displacement by an overall magnitude, the graphical object will respectively undershoot or overshoot the target location by an amount determined by the error factor.

Figure 12D:
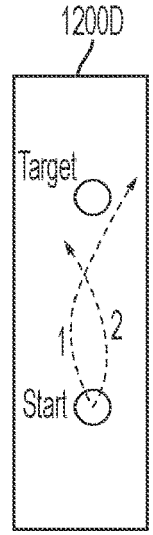
FIG. 12D is a schematic illustration of a GUI display of two example incorrect productions for the interactive visual story, according to one or more embodiments shown and described herein.
Figure 12E:
FIG. 12E is a schematic illustration of a GUI display of an unsuccessful production screen of the interactive visual story, according to one or more embodiments shown and described herein.

FIGS. 12D-12E display screens respectively showing a variety of potentially unsuccessful tongue displacements to arrive at the goal location and an unsuccessful production resulting in not reaching the goal location yet still being provided with an encouraging message. FIG. 12D illustrates an incorrect productions mapping screen 1200D showing two example incorrect productions of tongue placement that would not lead to success for the interactive visual story of FIG. 12A. The hypothetical error trajectories are based on incorrect tongue sub-part displacements. FIG. 12E illustrates an unsuccessful production screen 1200E indicative of an error production of the user through an incorrect tongue placement and failure to reach the target in the interactive visual story of FIG. 12A. An unsuccessful production may result in a pilot appearing on the unsuccessful production screen 1200E with a message to encourage the user. In embodiments, grayscale ultrasound imaging associated with the trajectories of FIGS. 12C and 12E may be visible on an interface, such as on the interface of a clinician but not on the interface of the user. For example, an ultrasound image 1202E of the unsuccessful tongue production may be visible on a display presented to, for example, the clinician.

Before each sound production by a user, a feedback graphical object position may be reset to a pre-defined starting point on the GUI display of the interactive visual story as determined by relative tongue part coordinates at a tongue resting point, such as associated with a sustained midcentral vowel /ə/. In an embodiment, the tongue resting point may be defined by an Articulatory Range of Movement (ARM) test. A goal location may be mapped at a distance from the starting location or to desired coordinates for the tongue parts for a target centroid as may be determined from results of a cluster analysis as described herein, for example, or as otherwise determined and input for a particular sound sequence. As a user moves their tongue during production of a sound, the graphical object of the interactive visual story on the GUI display will move in proportion to displacement of tongue parts of the user. Errors in tongue part displacements will thus cause the trajectory of the graphical object to deviate from a desired path and miss the goal location. Further, graphical object motion will terminate with the end of each speech utterance by the user.

The visual stories may include the helicopter theme as described with respect to FIGS. 12A-12E. Alternative visual stories may include a basketball theme with instructions to shoot a ball through a hoop or a butterfly theme to fly a butterfly to a tree. Otherwise visual stories including a story and corresponding task based on a starting location and target goal are within the scope of this disclosure.

As described above and in embodiments, visual stories including gamification techniques may include scoring techniques to further engage and motivate the user. For example, correct sound productions may result in an increase of a score presented to the user (e.g., by 100 points), while an incorrect sound production would not increase the score. At intervals that may be set by, for example, a clinician, such as 1000 point intervals, the scope passing a certain amount may cause the user to advance to a next, more difficult level. When advancing to a next level, a gain parameter associated with sub-part tongue displacement signals may be increased to make the task presented more challenging of the user.

The GUI displays described herein may be configured to display data in both tabular and graphical form on tongue part displacements, including both overall magnitudes and variations over time. The GUI displays described herein may further be configured to display and present acoustic records of sound production correlated with timing of displacements, distances of a user's sound productions from the biofeedback targets as, for example, a global performance metric, ultrasound images of the user's tongue showing ROIs and identified brightness maxima as described herein, and/or a means to rate a quality of sound production during each interactive visual story session. It is contemplated within the scope of this disclosure that the systems and methods described herein may be utilized with sounds beyond those of in English as described herein (e.g., beyond the /ar/ sound), including one or more sounds in any world language that involves a characteristic tongue shape. It is further contemplated within the scope of this disclosure that the systems and methods described herein may be utilized for various speech remediation treatments, including treatments of sound production disorders (e.g., RSSD) or to assist an individual with producing correct articulation in another language other than a native tongue (e.g., a second language).

It is further to be understood that while an ultrasound technology, which may include an ultrasound scanner, is described within respect to the systems and methods herein, such systems and methods may further be used with a clinical scanner based on a video output and processing of a tongue. Further, processing of raw echo data, such as from beamformed scan lines, may be used rather than video data with the tongue-mapping algorithms as described herein. Additionally, the systems and methods described herein are directed to the generation of one or more enhanced images of the tongue at least partially based on the plurality of US signals in real-time. The one or more enhanced images include identified Regions of Interest (ROIs) along tongue sub-parts comprising a tongue root, a tongue dorsum, and a tongue blade and respective ROI points identified therein. It is understood to correspondence that the generation of the one or more enhanced images is not a direct display of the images but rather corresponds to generation of a series of data points representative of spatial positions of a detected tongue surface along the tongue-air interface in space and time, which data points may further be reduced to positions or displacements of ROIs such as the tongue sub-parts described herein.

Figure 13:
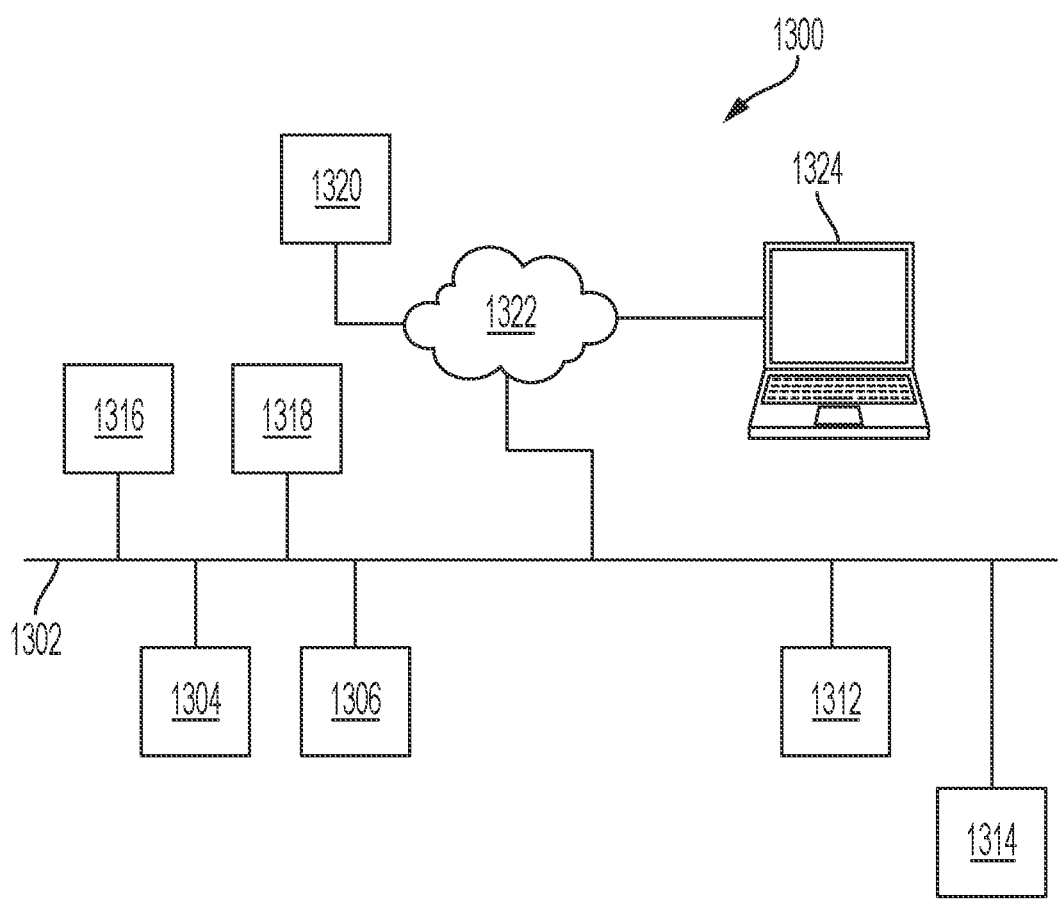
FIG. 13 schematically illustrates a system for implementing computer and software based methods to utilize the systems and methods of FIGS. 1-12E, according to one or more embodiments shown and described herein.

Referring to FIG. 13, a system 1300 for implementing a computer and software-based method for use of an enhanced ultrasound biofeedback therapy (UBT) system for an improved treatment of residual speech sound disorder (RSSD) is illustrated and may be implemented along with using a graphical user interface (GUI) 1324 that is accessible at and associated with a user workstation, e.g., a computing device, for example. The system 1300 includes a communication path 1302, one or more processors 1304, one or more memory components 1306 as one or more memory modules, an ultrasound component 1312, a storage or database 1314, a tongue-mapping component 1316, a network interface hardware 1318, a server 1320, a network 1322, and at least one GUI 1324. The various components of the system 1300 and the interaction thereof will be described in detail below.

In some embodiments, the system 1300 is implemented using a wide area network (WAN) or network 1322, such as an intranet or the Internet, or other wired or wireless communication network such as a local area network (LAN) or a cloud computing-based network configuration. The lines depicted in FIG. 11 indicate communication rather than physical connections between the various components.

As noted above, the system 1300 includes the communication path 1302. The communication path 1302 may be formed from any medium that is capable of transmitting a signal such as, for example, conductive wires, conductive traces, optical waveguides, or the like, or from a combination of mediums capable of transmitting signals. The communication path 1302 communicatively couples the various components of the system 1300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 1300 includes the one or more processors 1304. The one or more processors 1304 can be any device capable of executing machine readable instructions. Accordingly, the one or more processors 1304 may be a controller, an integrated circuit, a microchip, a computer, or any other computing device. The one or more processors 1304 is communicatively coupled to the other components of the system 1300 by the communication path 1302. Accordingly, the communication path 1302 may communicatively couple any number of processors with one another, and allow the modules coupled to the communication path 1302 to operate in a distributed computing environment. Specifically, each of the modules can operate as a node that may send and/or receive data. The one or more processors 1304 may process the input signals received from the system modules and/or extract information from such signals.

As noted above, the system 1300 includes the one or more memory components 1306 which is coupled to the communication path 1302 and communicatively coupled to the processor 1304. The one or more memory components 1306 may be a non-transitory computer readable medium or non-transitory computer readable memory and may be configured as a nonvolatile computer readable medium. The one or more memory components 1306 may comprise RAM, ROM, flash memories, hard drives, or any device capable of storing machine readable instructions such that the machine readable instructions can be accessed and executed by the one or more processors 1304. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the one or more memory components 1306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 1300 may include the one or more processors 1304 communicatively coupled to the one or more memory components 1306 that stores instructions that, when executed by the one or more processors 1304, cause the processor to perform one or more functions as described herein.

Still referring to FIG. 13, as noted above, the system 1300 comprises the display such as a GUI 1324 on a screen of a computing device for providing visual output such as, for example, information, ultrasound displays, graphical reports, messages, or a combination thereof. The display on the screen of the computing device is coupled to the communication path 1302 and communicatively coupled to the one or more processors 1304. Accordingly, the communication path 1302 communicatively couples the display to other modules of the system 1300. The display can include any medium capable of transmitting an optical output such as, for example, a cathode ray tube, light emitting diodes, a liquid crystal display, a plasma display, or the like.

The system 1300 comprises the ultrasound component 1312 that is coupled to the communication path 1302 and communicatively coupled to the one or more processors 1304 and configured to produce an ultrasound image for display on the GUI 1324. As will be described in further detail below, the one or more processors 1304 may process the input signals received from the system modules and/or extract information from such signals. The system 1300 further includes a tongue-mapping component 1316 configured to cooperate with the ultrasound component 1312 to produce an ultrasound image display of a tongue of a person with identified tongue region points of interest along a tongue-air interface as described herein.

The system 1300 includes the network interface hardware 1318 for communicatively coupling the system 1300 with a computer network such as network 1322. The network interface hardware 1318 is coupled to the communication path 1302 such that the communication path 1302 communicatively couples the network interface hardware 1318 to other modules of the system 1300. The network interface hardware 1318 can be any device capable of transmitting and/or receiving data via a wireless network. Accordingly, the network interface hardware 1318 can include a communication transceiver for sending and/or receiving data according to any wireless communication standard. For example, the network interface hardware 1318 can include a chipset (e.g., antenna, processors, machine readable instructions, etc.) to communicate over wired and/or wireless computer networks such as, for example, wireless fidelity (Wi-Fi), WiMax, BLUETOOTH®, IrDA, Wireless USB, Z-Wave, ZigBee, or the like.

Still referring to FIG. 13, data from various applications running on one or more computing devices associated with the GUI 1324 can be provided from the devices to the system 1300 via the network interface hardware 1318. The computing device can be any device having hardware (e.g., chipsets, processors, memory, etc.) for communicatively coupling with the network interface hardware 1318 and a network 1322. Specifically, the computing device can include an input device having an antenna for communicating over one or more of the wireless computer networks described above.

The network 1322 can include any wired and/or wireless network such as, for example, wide area networks, metropolitan area networks, the Internet, an Intranet, the cloud, satellite networks, or the like. Accordingly, the network 1322 can be utilized as a wireless access point by the one or more computing devices to access one or more servers (e.g., a server 1320). The server 1320 and any additional servers generally include processors, memory, and chipset for delivering resources via the network 1322. Resources can include providing, for example, processing, storage, software, and information from the server 1320 to the system 1300 via the network 1322. Additionally, it is noted that the server 1320 and any additional servers can share resources with one another over the network 1322 such as, for example, via the wired portion of the network, the wireless portion of the network, or combinations thereof.

For the purposes of describing and defining the present disclosure, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A system for an ultrasound biofeedback therapy for a speech remediation treatment for an individual through a user interface, the system comprising:
   one or more processors;
   one or more memory modules communicatively coupled to the one or more processors;
   an ultrasound machine comprising a display and communicatively coupled to the one or more memory modules;

a probe device communicatively coupled to the ultrasound machine, the probe device comprising a transducer;

a user interface module communicatively coupled to the display of the ultrasound machine, the user interface of a computing device, or both; and machine readable instructions stored in the one or more memory modules that cause the system to perform at least the following when executed by the one or more processors:

transmit a plurality of ultrasound (US) waves from the probe device toward a tongue of the individual along a mid-sagittal plane from below a jaw area of the individual;

receive, into the transducer of the probe device, a plurality of reflected US waves; convert, via the probe device, the plurality of reflected US waves into a plurality of US signals;

transmit, via the probe device, the plurality of US signals to the ultrasound machine;

generate one or more images of the tongue at least partially based on the plurality of US signals in real-time, the one or more images including identified Regions of Interest (ROIs) along tongue sub-parts comprising a tongue root, a tongue dorsum, and a tongue blade and respective ROI points identified therein, wherein each of the tongue root, the tongue dorsum, and the tongue blade are anatomical sub-parts of the tongue;

through the user interface module, generate an interactive visual story for display on the user interface of the computing device; and update the interactive visual story in real-time with a tongue-mapping trajectory of the individual on the user interface based on the one or more images.

2. The system of claim 1, wherein the machine readable instructions stored in the one or more memory modules further cause the system to perform at least the following when executed by the one or more processors:

display the one or more images on the display of the ultrasound machine.

3. The system of claim 1, wherein the respective ROI points are disposed along a tongue-air interface and comprise one or more Root Points along the tongue root, one or more Dorsum Points along the tongue dorsum, and one or more Blade Points along the tongue blade.

4. The system of claim 3, wherein the instructions to generate the one or more images including the respective ROI points identified in the identified ROIs along tongue sub-parts comprising the tongue root, the tongue dorsum, and the tongue blade comprise instructions to:

place the identified ROIs along the tongue-air interface in one or more frames representative of individual static frames of the one or more images, smooth the one or more frames, identify one or more local brightness maxima within each ROI such that one or more brightest points occur at the tongue-air interface, and dispose the respective ROI points in each identified ROI along the one or more local brightness maxima representative of the tongue-air interface.

5. The system of claim 1, wherein the machine readable instructions stored in the one or more memory modules further cause the system to perform at least the following when executed by the one or more processors:

determine a successful sound production when the tongue-mapping trajectory comprising a multi-part trajectory of the tongue sub-parts matches a desired path comprising one or more defined targets, the desired path configured for display on the interactive visual story, and determine an unsuccessful sound production when the tongue-mapping trajectory fails to match the desired path on the interactive visual story.

6. The system of claim 5, wherein the desired path on the interactive visual story is based on one or more successful tongue displacements for a sound sequence stored in the one or more memory modules.

7. The system of claim 6, wherein the one or more successful tongue displacements are based on stored displacements of the tongue sub-parts.

8. The system of claim 6, wherein the one or more successful tongue displacements for the sound sequence are based on one or more sets of cluster analysis for the sound sequence.

9. The system of claim 5, wherein one or more adjustable feedback parameters are used to determine the successful sound production or the unsuccessful sound production.

10. The system of claim 9, wherein the one or more adjustable feedback parameters comprise a gain value representative of an amplitude associated with tongue part movements to an amount of visual motion on the display of the interactive visual story.

11. The system of claim 9, wherein the one or more adjustable feedback parameters comprise an error factor indicative of a coefficient to determine a magnitude of deviations of a graphical feedback object representative of the tongue in response to erroneous tongue part movements.

12. The system of claim 5, wherein:

the interactive visual story comprises a start location, a goal location, and a graphical feedback object, the start location and the goal location are disposed at ends of the desired path, and the graphical feedback object is representative of the tongue and configured to follow the tongue-mapping trajectory.

13. The system of claim 12, wherein:

the interactive visual story is gamified and configured to provide user score points when the tongue-mapping trajectory matches the desired path on the interactive visual story between the start location and the goal location.

14. The system of claim 13, wherein:

when a threshold of user score points is exceeded, the interactive visual story advanced to a subsequent level of increased difficulty such that a gain value is decreased, the gain value representative of an amplitude associated with tongue part movements to an amount of visual motion on the display of the interactive visual story.

15. A method for an ultrasound biofeedback therapy for a speech remediation treatment for an individual, the method comprising:

transmitting a plurality of ultrasound (US) waves from a probe device toward a tongue of the individual along a mid-sagittal plane from below a jaw area of the individual;

receiving, into a transducer of the probe device, a plurality of reflected US waves;

converting, via the probe device, the plurality of reflected US waves into a plurality of US signals;

transmitting, via the probe device, the plurality of US signals to an ultrasound machine;

generating one or more images of the tongue at least partially based on the plurality of US signals in real-time, the one or more images including identified Regions of Interest (ROIs) along tongue sub-parts comprising a tongue root, a tongue dorsum, and a tongue blade and respective ROI points identified therein, wherein each of the tongue root, the tongue dorsum, and the tongue blade are anatomical sub-parts of the tongue;

generating an interactive visual story for display on a display of a computing device communicatively coupled to the ultrasound machine; and updating the interactive visual story in real-time with a tongue-mapping trajectory of the individual on the display based on the one or more images.

16. The method of claim 15, wherein the respective ROI points are disposed along a tongue-air interface and comprise one or more Root Points along the tongue root, one or more Dorsum Points along the tongue dorsum, and one or more Blade Points along the tongue blade.

17. The method of claim 16, wherein generating the one or more images including the respective ROI points identified in the identified ROIs along tongue sub-parts comprising the tongue root, the tongue dorsum, and the tongue blade further comprises:

placing the identified ROIs along the tongue-air interface in one or more frames representative of individual static frames of the one or more images, smoothing the one or more frames, identifying one or more local brightness maxima within each ROI such that one or more brightest points occur at the tongue-air interface, and disposing the respective ROI points in each identified ROI along the one or more local brightness maxima representative of the tongue-air interface.

18. The method of claim 15, further comprising:

determining a successful sound production when the tongue-mapping trajectory comprising a multi-part trajectory of the tongue sub-parts matches a desired path comprising one or more defined targets, the desired path configured for display on the interactive visual story, and determining an unsuccessful sound production when the tongue-mapping trajectory fails to match the desired path on the interactive visual story.

19. The method of claim 18, further comprising:

gamifying the interactive visual story through providing user score points when the tongue-mapping trajectory matches the desired path on the interactive visual story between a start location and a goal location.

* * * * *

UNITED STATES PATENT AND TRADEMARK OFFICE
CERTIFICATE OF CORRECTION

| | |
|---|---|
| PATENT NO. | : 11,688,294 B2 |
| APPLICATION NO. | : 16/955120 |
| DATED | : June 27, 2023 |
| INVENTOR(S) | : Suzanne Boyce et al. |

It is certified that error appears in the above-identified patent and that said Letters Patent is hereby corrected as shown below:

On the Title Page

In page 2, Column 2, item (56), other publications, cite no. 8, before "Sound Errors;", delete "Speec" and insert --Speech--, therefor.

In the Specification

In Column 1, Line 23, please replace "DC0136681" with --DC136881--, therefor.

In Column 1, Line 23, please replace "DC01731" with --DC017301--, therefor.

In Column 5, Line 57, delete "/ad" and insert --/ar/--, therefor.

In Column 6, Line 59, before "sound", delete "In" and insert --/r/--, therefor.

In Column 8, Line 27, delete "/ad" and insert --/ar/--, therefor.

In Column 8, Line 28, delete "In," and insert --/r/,--, therefor.

In Column 8, Line 41, delete "/ad" and insert --/ar/--, therefor.

In Column 8, Line 42, delete "/ad" and insert --/ar/--, therefor.

In Column 8, Line 45, delete "In," and insert --/r/,--, therefor.

Signed and Sealed this
Ninth Day of January, 2024

Katherine Kelly Vidal
*Director of the United States Patent and Trademark Office*